(12) United States Patent
Lewis et al.

(10) Patent No.: US 6,877,389 B2
(45) Date of Patent: Apr. 12, 2005

(54) DEVICE FOR REMOTE INSPECTION OF STEAM GENERATOR TUBES

(75) Inventors: Randall K. Lewis, Fairport, NY (US); William J. Harris, Farmington, NY (US); Katherine J. Steinke, Rochester, NY (US)

(73) Assignee: R. Brooks Associates, Inc., Williamson, NY (US)

( * ) Notice: Subject to any disclaimer, the term of this patent is extended or adjusted under 35 U.S.C. 154(b) by 269 days.

(21) Appl. No.: 10/341,601

(22) Filed: Jan. 14, 2003

(65) Prior Publication Data

US 2003/0169419 A1 Sep. 11, 2003

Related U.S. Application Data

(60) Provisional application No. 60/347,334, filed on Jan. 14, 2002.

(51) Int. Cl.⁷ .............................................. G01D 21/00
(52) U.S. Cl. ..................................................... 73/866.5
(58) Field of Search ............................ 73/865.8, 866.5; 356/241.1, 241.5, 241.6; 348/82–84; 324/220, 228, 234, 240

(56) References Cited

U.S. PATENT DOCUMENTS

| | | | |
|---|---|---|---|
| 3,994,173 A | 11/1976 | Ward et al. | |
| 4,317,632 A | 3/1982 | Orphan et al. | |
| 4,586,079 A | * | 4/1986 | Cooper et al. ................ 348/82 |
| 4,638,667 A | 1/1987 | Zimmer et al. | |
| 4,901,578 A | 2/1990 | Brill, III | |
| 4,955,235 A | 9/1990 | Metala et al. | |
| 5,025,215 A | 6/1991 | Pirl | |
| 5,105,876 A | 4/1992 | Burack et al. | |
| 5,174,164 A | 12/1992 | Wilheim | |
| 5,174,165 A | 12/1992 | Pirl | |
| 5,254,944 A | 10/1993 | Holmes et al. | |
| 5,279,168 A | 1/1994 | Timm | |
| 5,313,838 A | 5/1994 | Gondard et al. | |
| 5,963,030 A | 10/1999 | Stark | |
| 5,982,839 A | 11/1999 | Hatley | |
| 6,263,747 B1 | * | 7/2001 | Carson et al. ............. 73/866.5 |
| 6,282,943 B1 | * | 9/2001 | Sanders et al. ............. 73/23.2 |
| 6,357,310 B1 | 3/2002 | Blanchet et al. | |
| 6,532,839 B1 | 3/2003 | Kluth et al. | |

OTHER PUBLICATIONS

International Search Report (Dated Jun. 4, 2003).

* cited by examiner

Primary Examiner—Robert Raevis
(74) Attorney, Agent, or Firm—Nixon Peabody LLP

(57) ABSTRACT

A remote inspection device for the inspection of the tubesheet in-bundle region of a steam generator. The device includes a rail system that is easily and quickly mounted to the end of tube at an in-bundle region of a steam generator, a carriage movable on the rail system for feeding at flexible, tape-like wand into the tube, and a probe mounted on an end of the flexible, tape-like wand for performing the inspection operation. The flexible, tape-like wand, which is composed of a flexible metal alloy, has a non-circular center section forming a channel for receiving cabling for the probe and opposed flat, wings on either side of the non-circular center section. Each wing has a row of feed holes positioned remote from the center section that provide engagement with a feed wheel of the carriage.

9 Claims, 4 Drawing Sheets

DEVICE FOR REMOTE INSPECTION OF STEAM GENERATOR TUBES

CROSS REFERENCE TO RELATED APPLICATIONS

This application is related, under 35 U.S.C. 119(e), to Provisional Application No. 60/347,334 filed Jan. 14, 2002, the entire disclosure of which is hereby incorporated by reference.

BACKGROUND OF THE INVENTION

1. Field of the Invention

The present invention relates to devices for inspecting the in-bundle region of a steam generator above the tubesheet. The in-bundle region is comprised of two hemispherical regions extending from the second row of tubes beyond the last row of tubes and into the annulus on each side of the tubelane. Providing an ability to remotely inspect the in-bundle region on the top of the tubesheet is an important element of any steam generator maintenance program. The principle reasons for inspecting the in-bundle region include the need for monitoring the effectiveness of sludge lancing operations, for determining the trend fouling of the tubesheet and tube surfaces, for confirming potential loose parts identified through the eddy current inspection program and for searching and retrieving foreign objects.

2. Description of Related Art

Devices for inspecting the exterior walls of conduits such as the heat exchanger tubes of a steam generator are known in the prior art, for example in U.S. Pat. Nos. 5,982,839 and 5,963,030, the disclosures of which are hereby incorporated by reference. Additionally, devices for inspecting the interior walls of heat exchanger tubes of a steam generator are known in the prior art, for example in U.S. Pat. Nos. 6,357,310, 5,254,944, 5,313,838, 4,901,578 and 3,994,173, the disclosures of which are hereby incorporated by reference. Generally, such devices have included ultrasonic probes, and/or eddy current probes to inspect the walls of tubes for flaws, as shown in U.S. Pat. Nos. 5,105,876, 5,025,215 and 4,955,235, the disclosures of which are also hereby incorporated by reference. However, before the purpose and operation of such inspecting devices may be fully appreciated, some knowledge of the structure, operation and corrosion degradation problems associated with the heat exchanger tubes in steam generators is necessary.

Nuclear steam generators are comprised of three principal parts, including a secondary side, a tubesheet, and a primary side which circulates water heated from a nuclear reactor. The secondary side of the generator includes a plurality of U-shaped heat exchanger tubes, as well as an inlet for admitting a flow of water. The inlet and outlet ends of the U-shaped tubes within the secondary side of the generator are mounted in the tubesheet which hydraulically isolates the primary side of the generator from the secondary side. The primary side in turn includes a divider sheet which hydraulically isolates the inlet ends of the U-shaped tubes from the outlet ends. Hot water flowing from the nuclear reactor is admitted into the section of the primary side containing all of the inlet ends of the U-shaped tubes. This hot water flows through these inlets, up through the tubesheet, and circulates around the U-shaped tubes which extend within the secondary side of the generator. This water from the reactor transfers its heat through the walls of the U-shaped heat exchanger tubes to the non-radioactive feedwater flowing through the secondary side of the generator, thereby converting feedwater to non-radioactive steam which in turn powers the turbines of an electric generator. After the water from the reactor circulates through the U-shaped tubes, it flows back through the tubesheet, through the outlets of the U-shaped tubes, and into the outlet section of the primary side, where it is recirculated back to the nuclear reactor.

Over a period of time, sludge may accumulate in the annular spaces between the heat exchanger tubes and the tubesheet or support plates which surround them. Despite the fact that the heat exchanger tubes are formed from a corrosion-resistant alloy such as Inconel RTM™, these corrosive chemicals, in combination with the hot water which flows around such tubes, may cause a number of different forms of corrosion degradation. If unchecked, such corrosion may ultimately result in fissures in the walls of the tubes, which can cause water leakage through the walls of these tubes. In addition to reducing the efficiency of the steam generator as a whole, such leakage may cause radioactive elements carried by the water from the primary side of the generator to contaminate the non-radioactive water in the secondary side, thereby rendering the steam created by the generator undesirably radioactive.

In order to prevent such corrosion degradation from creating leaks in the heat exchanger tubes, a number of maintenance procedures have been developed, such as "sleeving" and "plugging" of badly corroded tubes. In order to repair tubes at the earliest possible states of corrosion and to thereby avoid the necessity of plugging tubes, both elongate ultrasonic probes and eddy current probes have been used to inspect the exteriror and interior walls of such heat exchanger tubes for degradation which indicates the beginning of a corrosive pattern.

Unfortunately, each type of external and internal inspection device is limited in its ability to be easily and efficiently positioned at the site of the small-diameter tubes in a nuclear steam generator while still being capable of perfectly informing the operator of the size, shape and type of a corrosion-induced flaw in a small-diameter tube of a nuclear steam generator. Probes attached to elongate feed cables of various designs are well known for inspecting the interior of a tube, as illustrated in U.S. Pat. Nos. 5,279,168, 5,174,165 and 5,174,164, the disclosures of which are hereby incorporated by reference. However, each of these systems involve feed and cable assemblies which are elaborate and cumbersome to install at the site and do not enable inspection of the exterior of the tubing of an in-bundle region. Further, the underlying need driving remote inspection operation of small diameter tubes in a nuclear steam generator is the reduction of human radiation exposure. Manual operation of inspection and retrieval devices from in front of steam generator hand-holes is radiation dose intensive work. As a consequence, anticipated high radiation exposure often causes service utilities to decide to leave foreign objects in their steam generators and to entirely exclude the top of tubesheet visual inspections from their inspection plans. Further, with the implementation of risk informed eddy current programs which allow extension of inspection intervals beyond one operating cycle, there is the necessity to satisfy regulatory concerns over loose part-induced tube leaks when skipping eddy current inspections for one or more cycles.

Clearly, there is a need for a remote, small-diameter tube inspecting device which is small enough to be used for inspecting the exterior of tubes in a tubesheet in the heat exchanger tubes of a nuclear steam generator which is capable of detecting flaws in the walls of these tubes with a higher degree of accuracy and reliability than previously achieved. Ideally, such an inspection device would be capable of being easily assembled at the work site, be capable of being quickly and efficiently positioned between the small-diameter tubes, and be capable of resolving all types of flaws, regardless of shape or orientation, as well as areas where the walls have been uniformly thinned by corrosion. Finally, such a device should be reliable in operation, and relatively easy to manufacture from commercially available components. These wide variety of constraints for remote inspection has generated many conflicting functional requirements which has led to fairly complex remote inspection devices as illustrated above.

SUMMARY OF THE INVENTION

The object of the present invention is to provide a remote inspection device which satisfies a broad range of remote in-bundle, top of tubesheet functional inspection requirements. That is, the remote inspection device of the invention is to provide a device that is easy to handle and assemble for installation and removal at the work site. Further, the remote inspection device of the invention utilizes conventional, commercially available parts, such as the rail from the Westinghouse Sludge Lancing Tool and video fiberscopes from Instrument Technology, Inc., and still further, the remote inspection device of the invention is waterproof and is capable of use in the secondary side of the steam generator after shutdown. The remote inspection device of the invention also can operate in a wide variety of conditions, i.e., relative humidity of 0 to 100%, temperatures of 40–120° F., and radiation up to 50 R/hr.

Further, another object of the remote inspection device of the invention is to enable remote inspecting of the exterior of tubes in a tubesheet to produce high quality images by being efficiently positioned to provide maximum inspection capability without damaging, i.e., scratching or denting, the tubes in any way.

Still another object is to provide a remote inspection device that is capable of inspecting both the square and triangular pitch steam generators without the need for a center stayrod, blowdown pipe, or tubelanc blocking devices; while also being capable of retrieving loose objects found during inspection. Further, the remote inspection device of the invention provides feedback as to its position within the tube bundle, and each component is designed for easy maintenance or replacement. The remote inspection device is also designed such that it will retract, in emergency situations, to a position which allows the assembly to be quickly and completely removed from the steam generator.

Finally, the preferred object of the present invention is provide a device capable of visually inspecting and retrieving objects from the in-bundle region on the top of the tubesheet of a steam generation system, such as that of Westinghouse Models 44F, 51F, 51A, 54F, F steam generators, Framatome models 51M, 51B, 51Bi, 47/22, 63/19, 73/19 steam generators, and BWI replacement and CE models.

The present invention provides a device of a simple design that can be quickly set up, and an inspection system that can be remotely operated to minimize time on a steam generator platform. The device of the invention will permit integration with other in-bundle tools such as the Westinghouse Sludge Lancing Tool system.

DETAILED DESCRIPTION OF THE INVENTION

Figure 1:
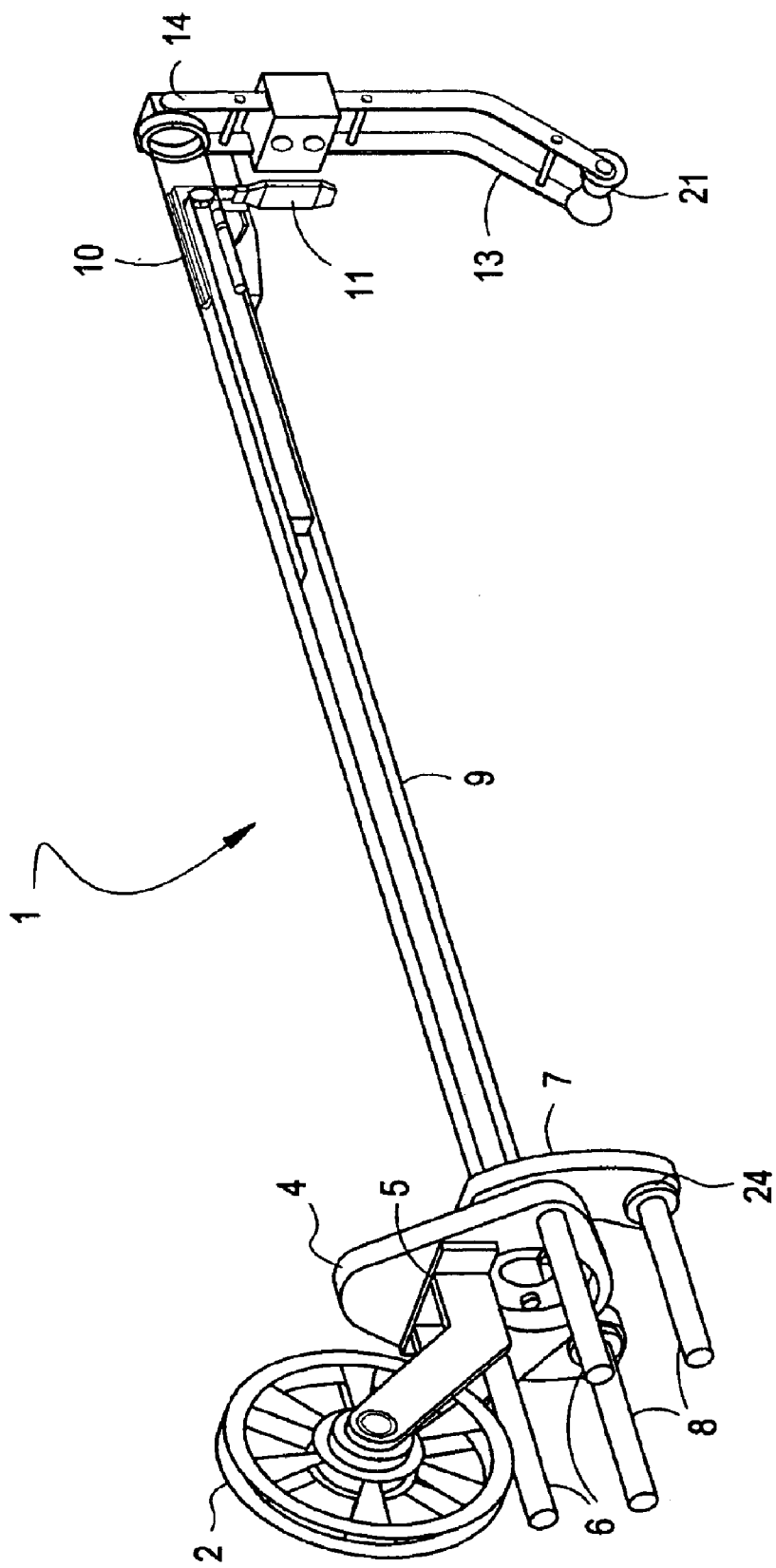
FIG. 1 illustrates a remote inspection device according to the invention.

The remote inspection device 1 of FIG. 1 illustrates a preferred embodiment of the invention which is attached to a handhole of a steam generator for positioning of a probe in a column between the tubes for inspecting the exterior surfaces of the tubes and their interface with the tubesheet. The device 1 includes a take-up reel 2, for a flexible wand 3 shown in FIG. 2, which is mounted on a motor support plate 4 via a pair of reel support brackets 5. The motor support plate 4 supports a motor (not shown) and includes a pair of elongated alignment pins 6 for aligned positioning of the remote inspection device to the handhole of the steam generator. Upon assembly at the handhole, the motor support plate 4 is clamped on the U-shaped rail support plate 7. The clamping is accomplished using elongated locking pins 8 which lock to openings in the support plate 7 and the handhole. Secured to the opposite side of the support plate 7 is a rail 9 which can be generally U- or L-shaped. The rail 9 supports a carriage 10, shown in detail in FIG. 3, which receives the flexible wand 3 from the take-up reel 2. At the lead end of the flexible wand 3 an inspection probe 11 is attached. The preferred probe 11 is video probe in the custom housing shown. The probe 11 also includes a fiber-optic cable (not shown) that is threaded in the channel 12 of the flexible wand 3. However, instead of the preferred video probe other types of probes can be employed with the remote inspection device of the invention. Examples of other types of probes are transducer and eddy-current sensor probes, as shown in U.S. Pat. No. 4,955,235, and a fiber-optic video probe as sold by Instrument Technology, Inc. At the distal end of the rail 9, a kickstand 13 is mounted, via pin 14, to pivot away from a position in alignment with the longitudinal axis of the rail 9 to a position away from (transverse) the longitudinal axis of the 9, as shown in FIG. 1. Upon complete insertion in the tubelane above the tubesheet, the kickstand 13 will drop into the transverse position adjacent the surface of the tube enclosing the tubesheet bundle or a center stayrod so that the guiding wheel 21, located at the remote end of the kickstand 13, contacts the tubesheet (not shown).

Figure 2:
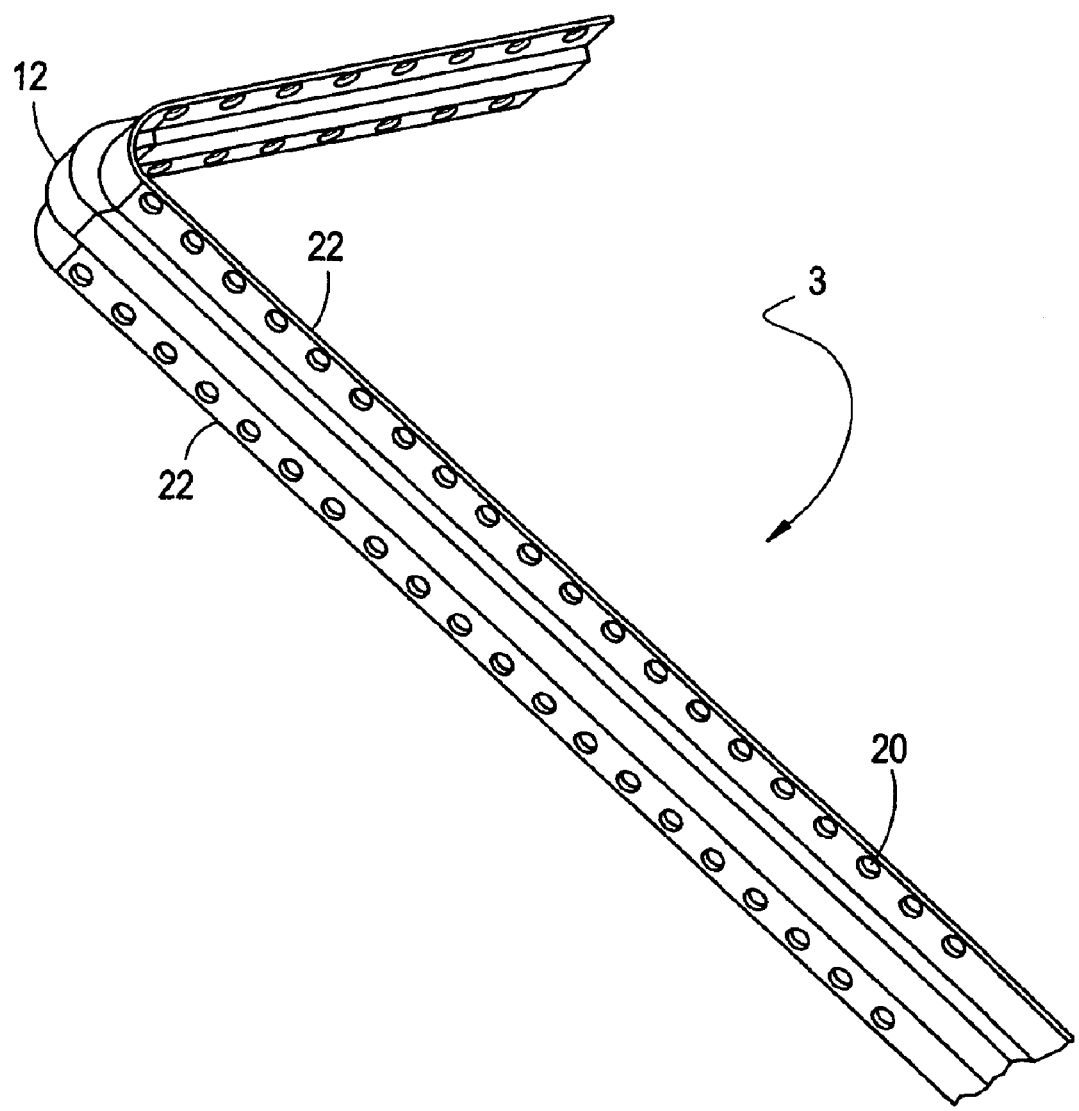
FIG. 2 illustrates a flexible wand of the invention.
Figure 3:
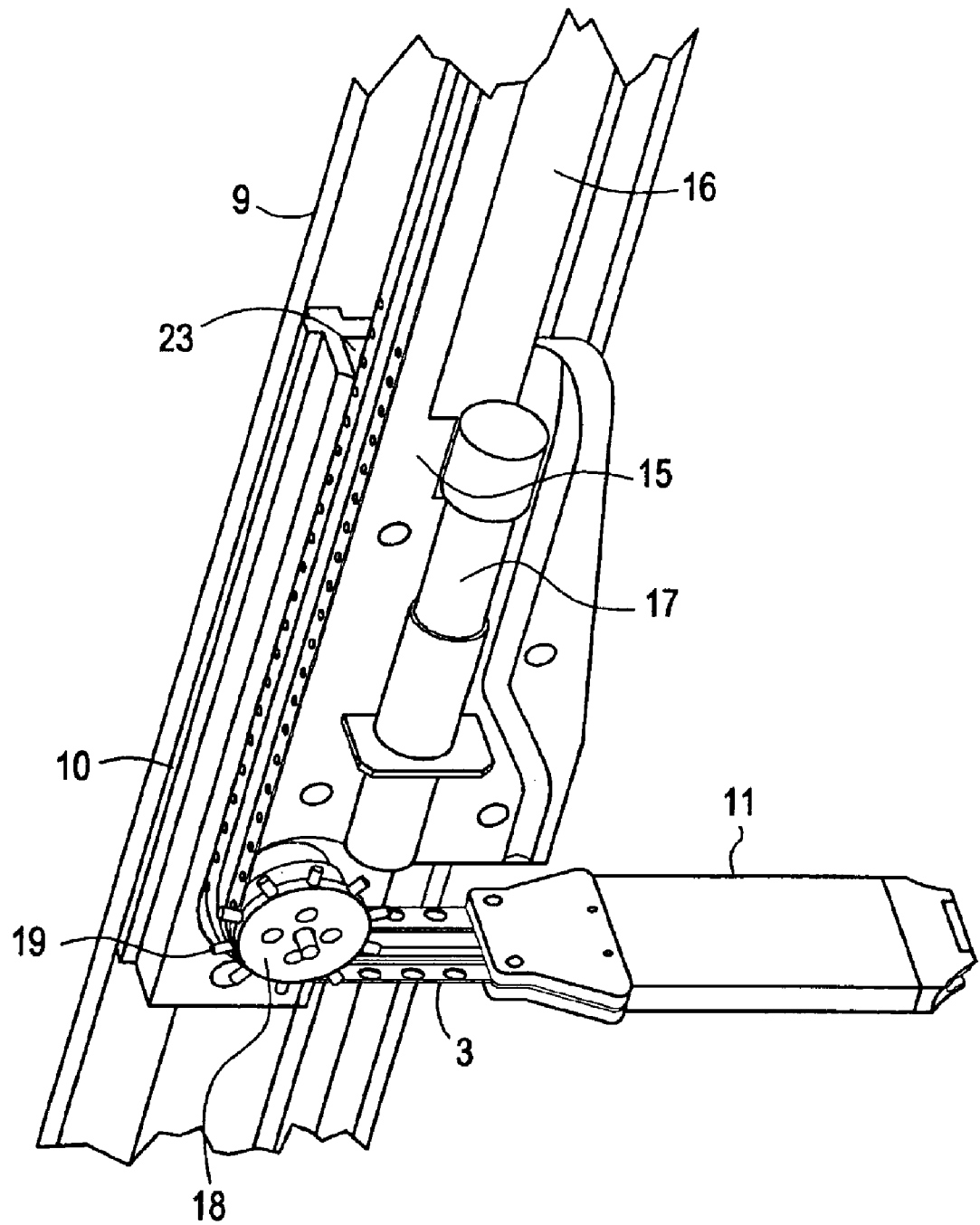
FIG. 3 illustrates a carriage assembly of the invention.

As shown in FIG. 3, the carriage 10 is positioned on the rail 9 such that the carriage 10 is guided along the rail. The precise positioning of the carriage 10 on the rail 9 is performed by a carriage mover 15 secured to the carriage and attached to drive rod mechanism 16, which is attached to the motor (not shown) on the motor support plate. An example of a drive rod mechanism for use in the present invention is a conventional screw-type rod used in garage door openers. In order to properly feed the flexible wand 3 between the tubes in the in-bundle region, the carriage 10 is provided with a remotely controlled indexing motor 17 connected to an indexing wheel 18 mounted for rotation on the carriage 10. The indexing wheel has at least one set of circumferentially spaced apart indexing pins 19 on its perimeter. The indexing pins matingly engage indexing holes 20, shown in FIGS. 2 and 4, in the flexible wand 3, for precise feeding of the probe 11 and flexible wand 3 between the tubes.

Figure 4:
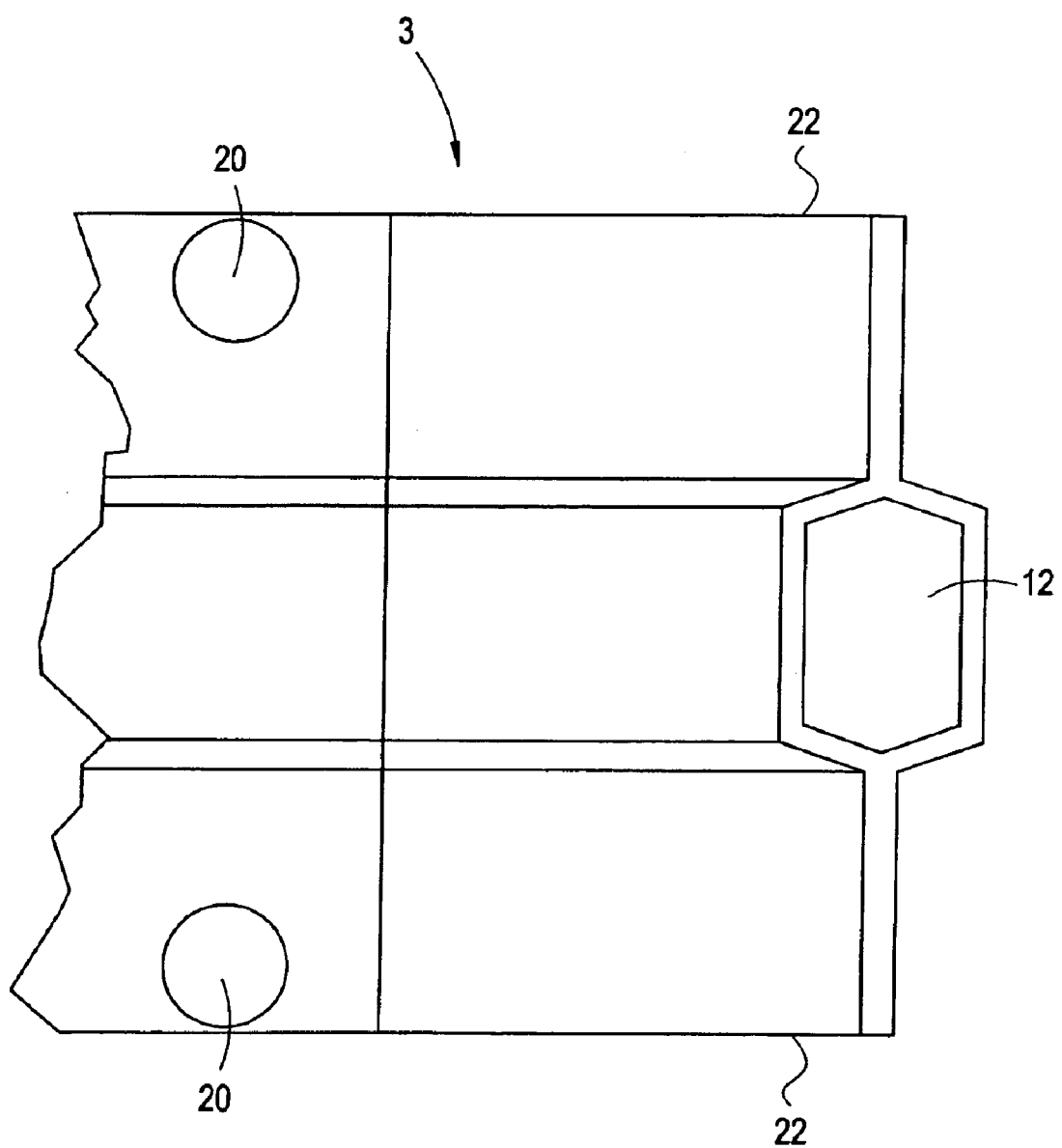
FIG. 4 illustrates the cross-section of a flexible wand of the invention.

A preferred embodiment of the flexible wand 3 of the invention, shown in FIGS. 2 and 4, is made of highly flexible metal strip (alloy) material, such as Nitinol™ or 400 Series Stainless. The wand 3 includes non-circular a center section forming a channel 12 for receipt of probe cabling (not shown) and also includes two integrally formed, longitudinally extending and opposed, flat wings 22 on either side of the non-circular center section 12. The wings 22 of the wand 3 are guided within a guide channel 23 in the carriage 10 to the indexing wheel 18. Each wing 22 has a row of feed holes 20 extending along the length of the wing and positioned remote from the center section 12 that provide engagement with indexing pins 19 of the indexing wheel 18 of the carriage 10.

The installation and operation of the remote inspection device 1 of the invention described above is as follows. The cabling of the probe is threaded into the channel 12 of flexible wand 3 and the wand 3 is wound upon the take-up reel 2. Then an end of the flexible wand 3 is unwound from the reel 2 and threaded into the rail 9. The wand 3 is then threaded into the carriage 10 such that at least one indexing pin engages an alignment hole in a wing 22. The cabling for the probe is then attached to the probe 11 and the probe 11 is fixedly attached to the wand 3. Of course, these steps can be performed off-site, i.e., at the factory, in order to provide a pre-assembled unit at the work site.

Thereafter, through a handhole of a steam generator, the rail 9 with the longitudinally aligned kickstand 13 is inserted into a tubelane above a tubesheet. Upon the rail reaching the farthest extremity of the tubesheet, the kickstand 13 drops into a position transverse to the longitudinal axis of the rail such that the kickstand 13 is positioned adjacent the surface of the enclosing tube of the tubesheet bundle or a center stayrod. The guiding wheel 21, located at the remote end of the kickstand 13, then contacts the tubesheet. This process enables the rail assembly to be quickly positioned at the in-bundle region for remote inspection.

The rail assembly is mounted at the handhole of a steam generator by locating the elongate alignment pins 6 in adjacent openings at the handhole. The motor support plate 4 is then slid onto the alignment pins 6, and, thereafter, the elongate locking pins 8 are placed in openings 24 in the U-shaped rail support plate 7 and positioned in the lock position. This locks the U-shaped rail support plate 7 in a secure position and clamps the motor support plate 4 to the U-shaped rail support plate 7.

The inspection process can be begin by activating the carriage mover 15 to move the carriage 10 to a position for insertion of the probe into the column between the tubes of the steam generator. Then the remotely controlled indexing motor 17 is activated to move the probe 11 downward into the column between the tubes. The probe 11 is then activated to commence inspection of the exterior of the tubes and tubesheet (if necessary). Upon completion of the inspection, the remotely controlled indexing motor 17 raises the probe 11 to a starting position (shown in FIG. 3), and the carriage mover 15 moves the carriage 10 to the next location needing inspection. With the inspection device of the invention, the simple rail assembly permits quick mounting, securing and dismounting of the probe above the in-bundle region; while the separately movable tape-like flexible wand and carriage enables rapid removal of the probe to a starting position for subsequent re-positioning of the probe or removal of the inspection device from the handhole. The inspection device of the invention permits the inspection process to be easily and quickly performed without the need for the elaborate feed means or extendible rail boons of the prior art discussed above.

Many other modifications and variations of the present invention are possible to the skilled practitioner in the field in light of the teachings herein. For example, the probe can be replaced with a device for removing detected loose material observed on the exterior of the tubes or between the tubes. It is therefore understood that, within the scope of the claims, the present invention can be practiced other than as herein specifically described.

What is claimed is:

1. A device for the remote inspection of tubes comprising:

a longitudinally extending rail assembly having a proximate and distal end;

worksite mounting means attached to the proximate of the rail assembly;

an elongate flexible wand guided along the rail assembly;

a take-up reel attached to the worksite mounting means for windingly supporting one end of the elongate flexible wand;

a carriage means attached for longitudinal movement along the rail assembly; and an inspection probe attached to a second end of the elongate flexible wand, wherein the rail assembly includes an elongate rail having a kickstand attached at the distal end for pivotable movement from a position aligned with a longitudinal axis of the rail to a position transverse to the longitudinal axis of the rail, wherein the elongate, flexible wand includes a non-circular central section defining an elongate interior channel for receiving probe cabling and two opposed longitudinally extending flat wings on each side of the non-circular central section in which each wing has a longitudinal row of indexing holes formed therein positioned remote from the non-circular section, and wherein the carriage means receives the second end of the elongate, flexible wand and includes a drive means for indexed movement of the flexible wand from a direction along the longitudinal axis of the rail to a direction transverse to the longitudinal axis of the rail.

2. The device according to claim 1, wherein the drive means for indexed movement of the flexible wand includes an indexing motor connected to an indexing wheel which has at least one set of circumferentially spaced apart indexing pins for engaging the indexing holes of a longitudinally extending flat wing.

3. The device according to claim 1, wherein the elongate flexible web is made of flexible metal strips.

4. The device according to claim 3, wherein the elongate flexible web is made of Nitinol™ or 400 series stainless steel strips.

5. The device according to claim 1, wherein the carriage includes a carriage mover secured to the carriage which is connected to a drive rod mechanism extending within the rail along its longitudinal axis.

6. The device according to claim 1, wherein the probe is a fiber-optic video probe.

7. The device according to claim 1, wherein the probe includes a transducer.

8. The device according to claim 1, wherein the probe includes an eddy-current sensor.

9. The device according to claim 1, wherein the rail of a U-shape or L-shape configuration and the carriage and elongate flexible wand are supporting within the rail.

* * * * *